(12) United States Patent
Turner

(10) Patent No.: US 9,687,311 B2
(45) Date of Patent: Jun. 27, 2017

(54) GRIP FORCE NORMALIZATION FOR SURGICAL INSTRUMENT

(71) Applicant: INUITIVE SURGICAL OPERATIONS, INC., Sunnyvale, CA (US)

(72) Inventor: Michael Turner, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/150,002

(22) Filed: May 9, 2016

(65) Prior Publication Data
US 2016/0324590 A1    Nov. 10, 2016

Related U.S. Application Data

(63) Continuation of application No. 14/276,934, filed on May 13, 2014, now Pat. No. 9,387,045.

(60) Provisional application No. 61/823,107, filed on May 14, 2013.

(51) Int. Cl.
| | |
|---|---|
| G05B 15/00 | (2006.01) |
| G05B 19/00 | (2006.01) |
| A61B 34/00 | (2016.01) |
| A61B 17/28 | (2006.01) |
| A61B 34/30 | (2016.01) |
| A61B 34/37 | (2016.01) |
| A61B 34/35 | (2016.01) |

(Continued)

(52) U.S. Cl.
CPC .............. *A61B 34/77* (2016.02); *A61B 17/28* (2013.01); *A61B 17/29* (2013.01); *A61B 34/30* (2016.02); *A61B 34/35* (2016.02); *A61B 34/37* (2016.02); *A61B 34/76* (2016.02); *A61B 2090/065* (2016.02)

(58) Field of Classification Search
CPC ........ B25J 9/1689; B25J 9/1694; B25J 13/00; B25J 13/02; B25J 13/025; B25J 13/088; B25J 9/1633; G01L 5/22; A61B 19/2203; A61B 19/22; A61B 2019/2223; A61B 2019/2269
USPC .................. 700/245, 247, 253, 257, 260; 318/568.11, 568.12, 568.16, 568.21
See application file for complete search history.

(56) References Cited

U.S. PATENT DOCUMENTS

| | | |
|---|---|---|
| 6,331,181 B1 | 12/2001 | Tierney et al. |
| 6,493,608 B1 | 12/2002 | Niemeyer |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jaime Figueroa
(74) *Attorney, Agent, or Firm* — Jones Robb, PLLC

(57) ABSTRACT

A teleoperated surgical system includes a surgical instrument with an end effector and a master input device. A servomechanism may be operatively coupled to the end effector to apply a force to the end effector, and at least one processor may operatively couple the servomechanism to the master input device to apply a grip force with the first and second gripping elements in response to input at the (Continued)

master input device. The applied grip force may be based at least in part on a mechanical advantage of the surgical instrument end effector.

20 Claims, 14 Drawing Sheets

(51) Int. Cl.
    *A61B 17/29*    (2006.01)
    *A61B 90/00*    (2016.01)

(56) References Cited

U.S. PATENT DOCUMENTS

| | | | |
|---|---|---|---|
| 6,594,552 B1 * | 7/2003 | Nowlin | B25J 9/1689 318/568.11 |
| 6,671,581 B2 | 12/2003 | Niemeyer et al. | |
| 2005/0251110 A1 * | 11/2005 | Nixon | B25J 9/1692 606/1 |
| 2007/0144298 A1 * | 6/2007 | Miller | B25J 9/1676 74/490.01 |
| 2008/0046122 A1 * | 2/2008 | Manzo | A61B 1/00149 700/245 |
| 2008/0130965 A1 * | 6/2008 | Avinash | A61B 90/36 382/128 |
| 2010/0087835 A1 | 4/2010 | Blumenkranz et al. | |
| 2010/0228264 A1 * | 9/2010 | Robinson | A61B 18/1206 606/130 |
| 2010/0332031 A1 * | 12/2010 | Itkowitz | B25J 9/1689 700/245 |
| 2011/0071542 A1 | 3/2011 | Prisco et al. | |
| 2011/0118707 A1 * | 5/2011 | Burbank | A61B 34/30 606/1 |
| 2011/0282491 A1 * | 11/2011 | Prisco | A61B 34/71 700/258 |
| 2012/0215220 A1 * | 8/2012 | Manzo | A61B 18/1445 606/46 |
| 2013/0103050 A1 * | 4/2013 | Richmond | A61B 34/30 606/130 |
| 2014/0148819 A1 * | 5/2014 | Inoue | B25J 9/1612 606/130 |
| 2014/0148950 A1 * | 5/2014 | Ogawa | B25J 13/02 700/257 |
| 2014/0330434 A1 * | 11/2014 | Nixon | B25J 9/1692 700/254 |
| 2014/0343569 A1 | 11/2014 | Turner | |
| 2015/0053737 A1 * | 2/2015 | Leimbach | A61B 17/07207 227/175.1 |

* cited by examiner

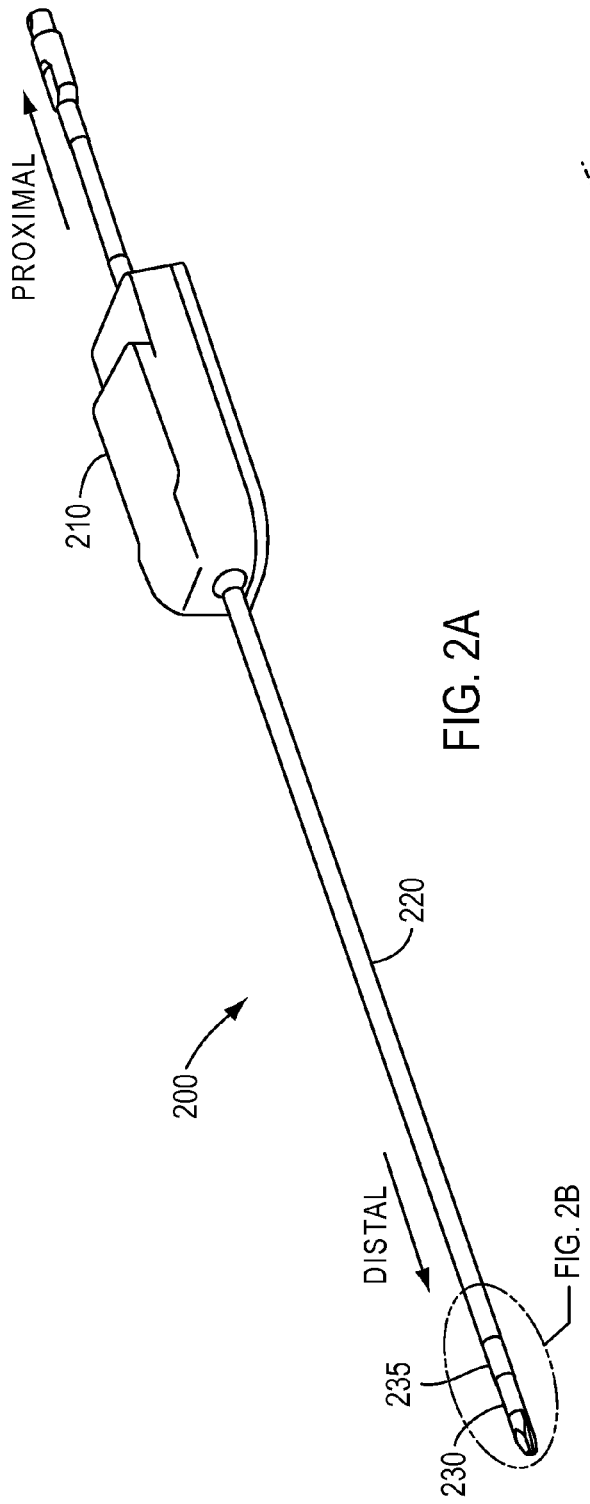
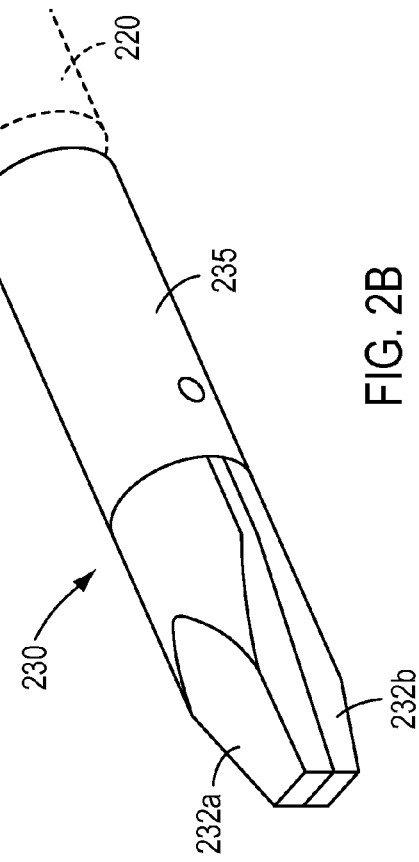
FIG. 2A
FIG. 2B

GRIP FORCE NORMALIZATION FOR SURGICAL INSTRUMENT

CROSS-REFERENCE TO RELATED APPLICATIONS

This application is a continuation of U.S. patent application Ser. No. 14/276,934, filed May 13, 2014, which claims priority to U.S. Provisional Application No. 61/823,107, filed May 14, 2013, the entirety of each of which is incorporated by reference herein.

TECHNICAL FIELD

The present disclosure is generally directed to controlling a surgical instrument end effector. More particularly, aspects of the present disclosure relate to controlling the gripping force of an end effector for a robotically-controlled (teleoperated) surgical instrument.

INTRODUCTION

Minimally invasive surgical techniques generally attempt to perform surgical procedures while minimizing damage to healthy tissue. Robotically-controlled (teleoperated) surgical instruments can be used to perform various minimally invasive surgical procedures remotely. In such systems, surgeons manipulate various input devices at a surgeon console (sometimes referred to herein as master inputs). The input at the surgeon console is communicated to a patient side cart that interfaces with one or more surgical instruments, where teleoperated/telerobotic manipulation of the surgical instrument occurs to perform a surgical and/or other procedure on the patient.

Minimally invasive, teleoperated surgical instruments may be used in a variety of operations and have various configurations. Many such instruments include a surgical end effector mounted at a distal end of a long shaft that is configured to be inserted (e.g., laparoscopically or thoracoscopically) through an opening (e.g., body wall incision, natural orifice) to reach a remote surgical site within a patient. In some instruments, an articulating wrist mechanism is mounted to the distal end of the instrument's shaft to support the end effector and alter an orientation (e.g., pitch and/or yaw) of the end effector with reference to the shaft's longitudinal axis.

Teleoperated end effectors may be configured to perform various functions, including any of a variety of surgical procedures that are conventionally performed in either open or manual minimally invasive surgical procedures. Examples include, but are not limited to, sealing, cutting, cauterizing, ablating, suturing, stapling, etc. The end effectors may include a gripping device, such as jaws or blades, in cases in which tissue may need to be grasped and held as a procedure is performed, for example, during sealing (e.g., via cauterizing) or cutting of the tissue. In some instances, the control of the gripping device of a surgical instrument end effector occurs through master grip input from a surgeon at the surgeon console. To control motion of an end effector, servo-actuators (e.g., servo motors), can be used to transmit force or torque to various components that ultimately interface with the surgical instrument, generally through a transmission housing, to transmit force down the instrument shaft and to the end effector.

For some surgical instrument end effectors having opposing jaws, the arrangement and manner of connection of the jaws may impact how force is transmitted to the end effectors, and how that force varies throughout a range of motion of the end effector jaws. There exists a need, therefore, to provide a normalized gripping force for a surgical instrument end effector gripping device throughout a range of motion of the end effector gripping device to permit functional utilization of the instrument throughout its range of motion.

SUMMARY

The present disclosure solves one or more of the above-mentioned problems and/or demonstrates one or more of the above-mentioned desirable features. Other features and/or advantages may become apparent from the description that follows.

In accordance with at least one exemplary embodiment, the present teachings contemplate a method for controlling grip force of an end effector of a teleoperated surgical instrument. The method comprises receiving a first input signal indicative of a commanded position of first and second gripping elements of the surgical instrument end effector. The method further comprises outputting an actuation signal in response to receiving the first input signal and second input signals to apply a grip force with the first and second gripping elements, the grip force based at least in part on a mechanical advantage of the surgical instrument end effector.

In accordance with another exemplary embodiment, the present teachings contemplate a teleoperated surgical system that includes a master input device including first and second input members, a surgical instrument having an end effector with first and second gripping elements, and a servomechanism operatively coupled to the end effector to apply a force to the end effector. The surgical system further includes at least one processor operatively coupling the servomechanism to the master input device to apply a grip force with the first and second gripping elements in response to input at the master input device, the grip force based at least in part on a mechanical advantage of the surgical instrument end effector.

Additional objects and advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the present teachings, as disclosed or claimed. The claims should be entitled to their full breadth of scope, including equivalents.

BRIEF DESCRIPTION OF THE DRAWINGS

The present disclosure can be understood from the following detailed description either alone or together with the accompanying drawings. The drawings are included to provide a further understanding of the present disclosure, and are incorporated in and constitute a part of this specification. The drawings, which are incorporated in and constitute a part of this specification, illustrate one or more embodiments of the present disclosure and, together with the description, serve to explain certain principles and operation. In the drawings.

FIG. 2A is a perspective view of a teleoperated surgical instrument in accordance with at least one exemplary embodiment of the present teachings;

FIG. 2B is an enlarged perspective view of the end effector of the surgical instrument of FIG. 2A in accordance with an exemplary embodiment of the present teachings;

DETAILED DESCRIPTION

Figure 1A:
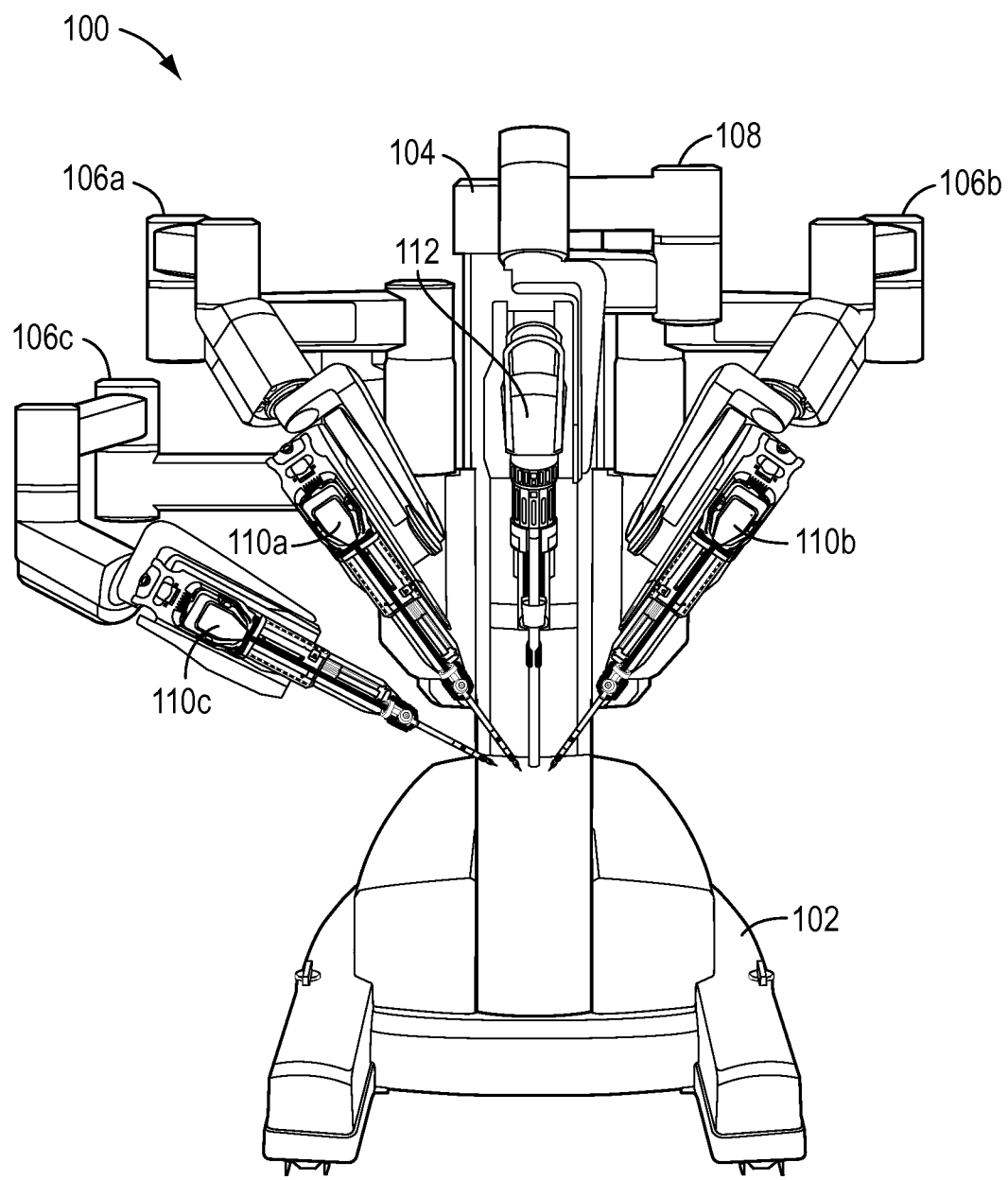
FIG. 1A is a front elevation, diagrammatic view of an exemplary patient side cart of a teleoperated surgical system.

This description and the accompanying drawings illustrate exemplary embodiments and should not be taken as limiting, with the claims defining the scope of the present disclosure, including equivalents. Various mechanical, compositional, structural, electrical, and operational changes may be made without departing from the scope of this description and the present teachings as claimed, including equivalents.

In some instances, well-known structures, and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or the surgical instrument.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Further, this description's terminology is not intended to limit the disclosure. The term "force" is to be construed as encompassing both force and torque, unless otherwise indicated herein or clearly contradicted by context. The terms "tools" and "instruments" are used interchangeably herein to refer to the surgical instruments. As used in this specification and the appended claims, the singular forms "a," "an," and "the," and any singular use of any word, include plural referents unless expressly and unequivocally limited to one referent. The terms "comprising," "having," "including," and "containing" are to be construed as open-ended terms (i.e., meaning "including, but not limited to,") unless otherwise noted. The terms "connected" and "coupled" are to be construed as partly or wholly contained within, attached to, or joined together, even if there is something intervening.

Spatially relative terms—such as "proximal" and "distal"—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, the terms "proximal" and "distal" are relative terms, where the term "distal" refers to the portion of the object furthest from an operator of the instrument and closest to the surgical site, such as the opening of the tool cover or the end effector of the instrument. The term "proximal" indicates the relative proximity to the operator of the surgical instrument and refers to the portion of the object closest to the operator and furthest from the surgical site. In this application, an end effector refers to a tool installed at the distal end of an instrument, including but not limited to forceps or graspers, needle drivers, scalpels, scissors, spatulas, blades, and other tools, which may or may not use energy to cauterize tissue (i.e., a monopolar or bipolar tool).

Figure 1B:
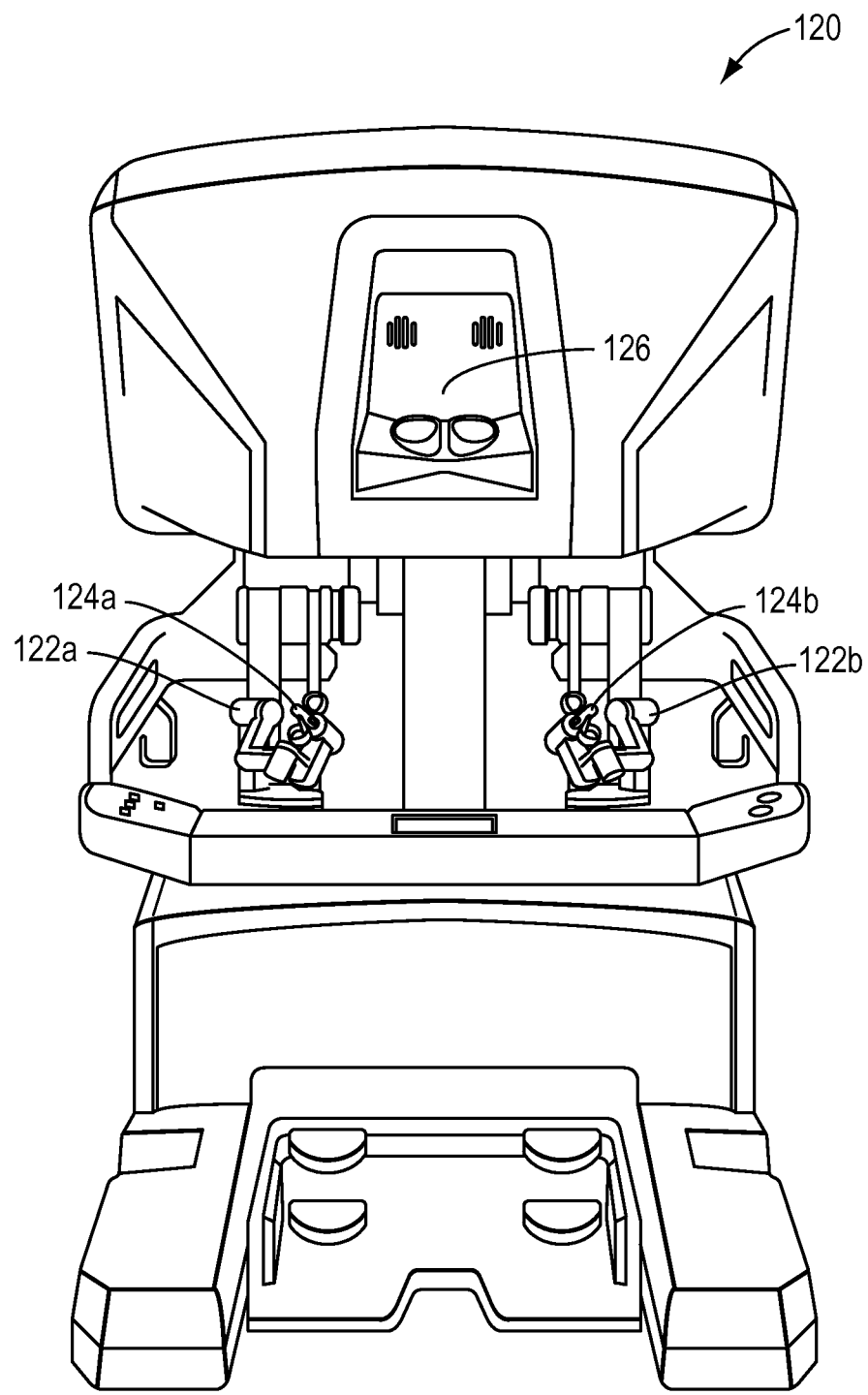
FIG. 1B is a front elevation, diagrammatic view of an exemplary surgeon's console of a teleoperated surgical system.
Figure 1C:
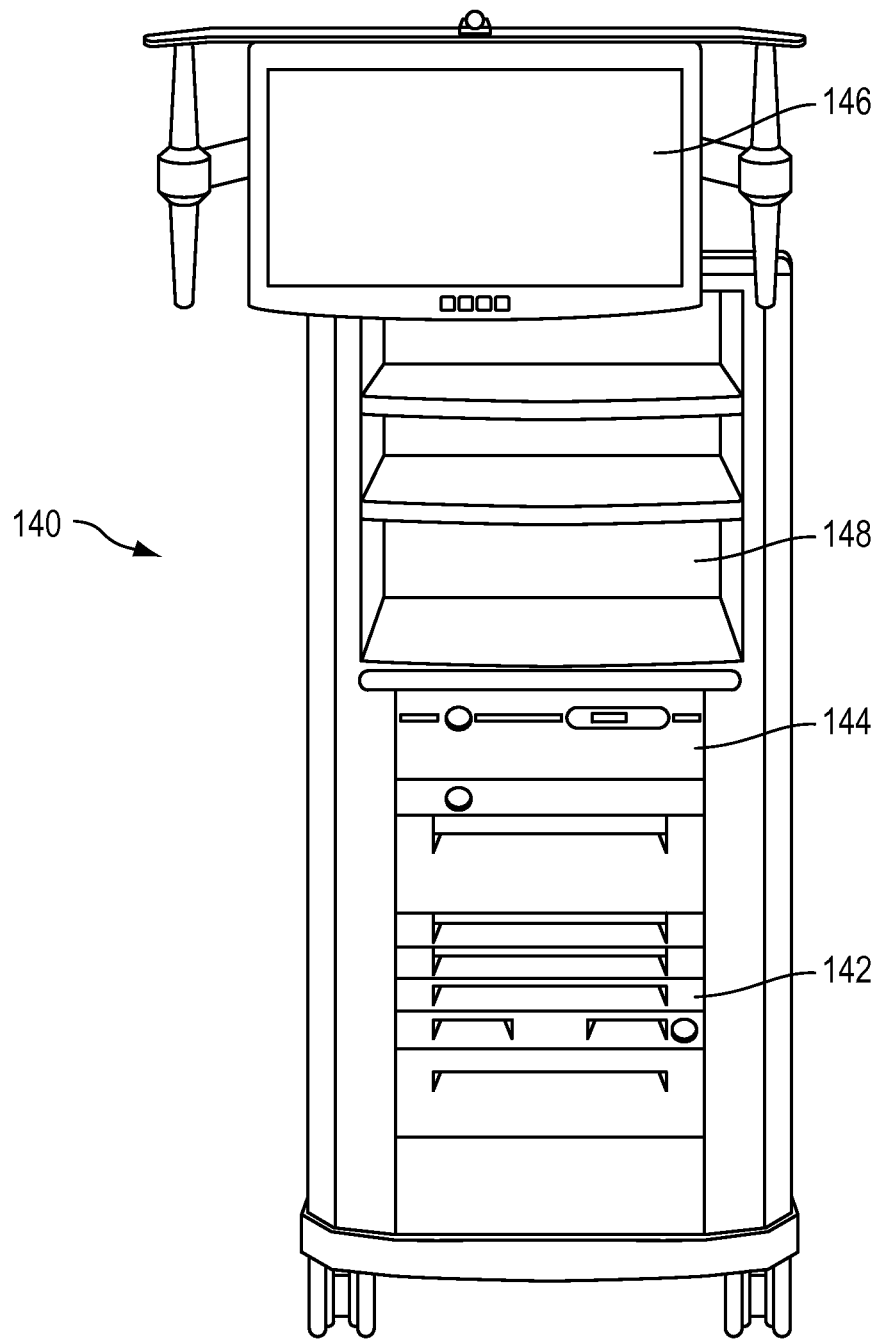
FIG. 1C is a front elevation, diagrammatic view of an exemplary auxiliary control/vision cart of a teleoperated surgical system.

FIGS. 1A, 1B, and 1C are front elevation views of three exemplary embodiments of main components of a teleoperated surgical system for minimally invasive surgery. These three components are interconnected so as to allow a surgeon, for example, with the assistance of a surgical team, to perform diagnostic and corrective surgical procedures on a patient. In an exemplary embodiment, a teleoperated surgical system in accordance with the present disclosure may be embodied as a da Vinci® surgical system commercialized by Intuitive Surgical, Inc. of Sunnyvale, Calif. Also, for a further explanation of a teleoperated surgical system, including a patient side cart, surgeon's console, and auxiliary control/vision cart, with which the present disclosure may be implemented, reference is made to U.S. Patent App. Pub. No. 2011/0071542 A1 (published Mar. 24, 2011), entitled "CURVED CANNULA SURGICAL SYSTEM," which is incorporated by reference in its entirety herein. However, the present disclosure is not limited to any particular surgical system, and one having ordinary skill in the art would appreciate that the disclosure herein may be applied in a variety of surgical applications, including other teleoperated surgical systems.

FIG. 1A is a front elevation view of an exemplary embodiment of a patient side cart 100 of a teleoperated surgical system. The patient side cart 100 includes a base 102 that rests on the floor, a support tower 104 mounted on the base 102, and one or more manipulator arms mounted on the support tower 104 and that support surgical instruments and/or vision instruments (e.g., a stereoscopic endoscope). As shown in FIG. 1A, manipulator arms 106a, 106b are arms that support, and transmit forces to manipulate, the surgical instruments used to grasp and move tissue, and arm 108 is a camera arm that supports and moves the endoscope. FIG. 1A also shows a third manipulator arm 106c that is supported on the back side of support tower 104 and that is positionable to either the left or right side of the patient side cart as desired to conduct a surgical procedure.

Interchangeable surgical instruments 110a, 110b, 110c can be installed on the manipulator arms 106a, 106b, 106c, and an endoscope 112 can be installed on the camera arm 108. Those of ordinary skill in the art will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Control of the robotic surgical system, including control of the surgical instruments, may be effectuated in a variety of ways, depending on the degree of control desired, the size of the surgical assembly, and other factors. In some embodiments, the control system includes one or more manually operated input devices, such as a joystick, an exoskeletal glove, pincher or grasper assemblies, buttons, pedals, or the like. These input devices control servo motors which, in turn, control the articulation of the surgical assembly. The forces generated by the servo motors are transferred via drivetrain mechanisms, which transmit the forces from the servo motors generated outside the patient's body through an intermediate portion of the elongate surgical instrument 110 to a portion of the surgical instrument inside the patient's body distal from the servo motor.

FIG. 1B is a front elevation view of an exemplary surgeon's console 120 of a teleoperated surgical system for controlling the insertion and articulation of surgical instruments 110. The surgeon or other system operator manipulates input devices by moving and repositioning input devices within console 120. As illustrated in the exemplary embodiment of FIG. 1B, the surgeon's console is equipped with master controllers or master input devices. As illustrated in FIG. 1B, master input devices may include left and right multiple degree-of-freedom (DOF) master tool manipulators (MTM's) 122a, 122b, which are kinematic chains that are used to control the surgical tools (which include the endoscope and various cannulas mounted on arms 106, 108 of the patient side cart 100). Each MTM may include an area for surgeon or operator input. For example, as shown in FIG. 1B, each MTM 122a, 122b may include a pincher assembly 124a, 124b. The surgeon grasps a pincher assembly 124a, 124b on each MTM 122a, 122b, typically with the thumb and forefinger, and can move the pincher assembly to various positions and orientations. When a tool control mode is selected, each MTM 122 is coupled to control a corresponding manipulator arm 106 for the patient side cart 100, as those of ordinary skill in the art are familiar. The pincher assembly is typically used to operate a surgical end effector (e.g., scissors, grasping retractor, needle driver, hook, forceps, spatula, etc.) at the distal end of an instrument 110.

Surgeon's console 120 also can include an image display system 126. In an exemplary embodiment, the image display is a stereoscopic display wherein left side and right side images captured by the stereoscopic endoscope 112 are output on corresponding left and right displays, which the surgeon perceives as a three-dimensional image on display system 126.

The surgeon's console 120 is typically located in the same operating room as the patient side cart 100, although it is positioned so that the surgeon operating the console may be outside the sterile field. One or more assistants may assist the surgeon by working within the sterile surgical field (e.g., to change tools on the patient side cart, to perform manual retraction, etc.). Accordingly, the surgeon may operate remote from the sterile field, and so the console may be located in a separate room or building from the operating room. In some implementations, two consoles 120 (either co-located or remote from one another) may be networked together so that two surgeons can simultaneously view and control tools at the surgical site.

FIG. 1C is a front elevation view of an exemplary auxiliary control/vision cart 140 of the teleoperated surgical system. The cart 140 houses the surgical system's central electronic data processing unit 142 (also referred to herein as a "processor" and a "controller", the terms being used interchangeably) and vision equipment 144. Although described as a "processing unit," it is to be appreciated that the processing unit or processor 142 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to auxiliary control/vision cart 140, the processing unit 142 may also comprise a number of subunits distributed throughout the system.

The central electronic data processing unit 142 includes much of the data processing used to operate the surgical system. The data, reprogrammable software, program method steps, and method steps described herein may be embodied in a machine readable code and stored as a tangible medium in a wide variety of differing configurations, including random access memory, non-volatile memory, write once memory, magnetic recording media, optical recording media, and the like. Along with software, at least some of the programming and data may be embodied in the form of hardware or firmware.

The central electronic data processing unit or processor 142 performs various functions in the system 100. One function that it may perform is to translate and transfer the mechanical motion of input devices 122, 124 through control signals so that the surgeon can effectively manipulate and otherwise move devices, such as the instrument 110, that are selectively associated with the input devices 122, 124 at the time.

For additional details on the construction and operation of general aspects of a teleoperated surgical system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," each of which is incorporated herein by reference in its entirety.

The vision equipment includes camera control units for the left and right image capture functions of the stereoscopic endoscope 112. The vision equipment also includes illumination equipment (e.g., Xenon lamp) that provides illumination for imaging the surgical site. As shown in FIG. 1C, the auxiliary control/vision cart 140 includes an optional display 146 (e.g., a touchscreen monitor), which may be mounted elsewhere, such as on the patient side cart 100. The auxiliary control/vision cart 140 further includes space 148 for optional auxiliary surgical equipment, such as electrosurgical units, insufflators, and/or other flux supply and control units. The patient side cart 100 (FIG. 1A) and the surgeon's console 120 (FIG. 1B) are coupled via optical fiber communications links to the auxiliary control/vision cart 140 so that the three components together act as a single teleoperated minimally invasive surgical system that provides an intuitive telepresence for the surgeon.

In accordance with various exemplary embodiments, the present disclosure contemplates controlling a surgical instrument such that a gripping force applied by an end effector of the instrument is substantially linear throughout a range of motion of the end effector for a given force applied to a push-pull (drive) rod of the instrument to actuate the end effector.

With reference to FIG. 2A, an exemplary embodiment of a teleoperated surgical instrument 200 is depicted. As shown in FIG. 2, the instrument 200 generally includes a proximal housing 210 at its proximal end; proximal housing 210 may include an instrument memory or storage device (not shown). The memory can perform a number of functions when the instrument is loaded on the manipulator arm 106. For example, the memory can provide a signal verifying that the instrument is compatible with that particular surgical system. Additionally, the memory may identify the instrument and end effector type (whether it is a scalpel, a needle grasper, jaws, scissors, a clip applier, an electrocautery blade, or the like) to the surgical system so that the system can reconfigure its programming to take full advantage of the instrument's specialized capabilities. As further discussed below, the memory may include specifics on the architecture of the instrument, and include particular values that should be employed in control algorithms, such as tool compliance and gain values.

Proximal housing 210 also may include a force/torque drive transmission mechanism (not shown) for receiving output from motors of the manipulator arm 106, the force/torque drive transmission mechanism transmitting the output from the motors to an end effector 230 of the instrument through an instrument shaft 220 mounted to the transmission mechanism. Exemplary surgical robotic instruments, instrument/manipulator arm interface structures, and data transfer between the instruments and servomechanism is more fully described in U.S. Pat. No. 6,331,181, entitled "Surgical Robotic Tools, Data Architecture, and Use", issued on Dec. 18, 2001, the full disclosure of which is incorporated herein by reference.

The end effector 230 is disposed at the distal end of the shaft 220 and may be connected thereto by a clevis 235 that supports and mounts the end effector 230 relative to the instrument shaft 220. As embodied herein, the shaft 220 may be a relatively flexible structure that can bend and curve. Alternatively, the shaft 220 may be a relatively rigid structure that does not permit traversing through curved structures. Optionally, in some embodiments, the instrument 200 also can include a multi-DOF articulable wrist structure (not shown) that supports the end effector 230 and permits multi-DOF movement of the end effector in arbitrary pitch and yaw. Those having ordinary skill in the art are familiar with a variety of wrist structures used to permit multi-DOF movement of a surgical instrument end effector.

As embodied herein, a variety of alternative end effectors may be used on surgical instrument 200. As illustrated in FIG. 2B, such end effectors may include first and second end effector elements 232a, 232b which pivot relative to each other so as to define a pair of end effector jaws. In some embodiments, the tools or end effectors can be recognized by the system through reading of a memory mounted on the tool make use of a memory structure mounted on the tool.

Figure 3A:
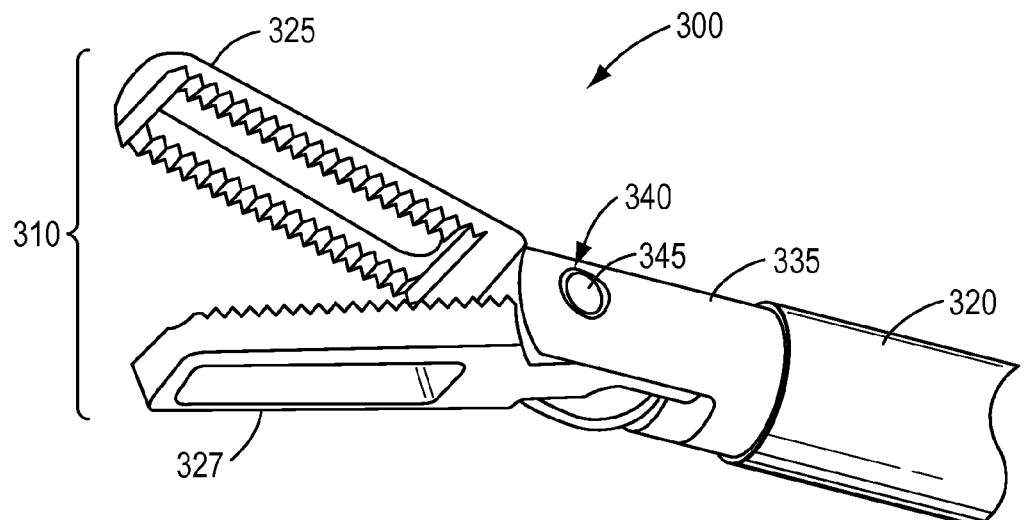
FIG. 3A is a perspective view of an exemplary end effector a teleoperated surgical instrument in accordance with another exemplary embodiment of the present teachings.
Figure 3B:
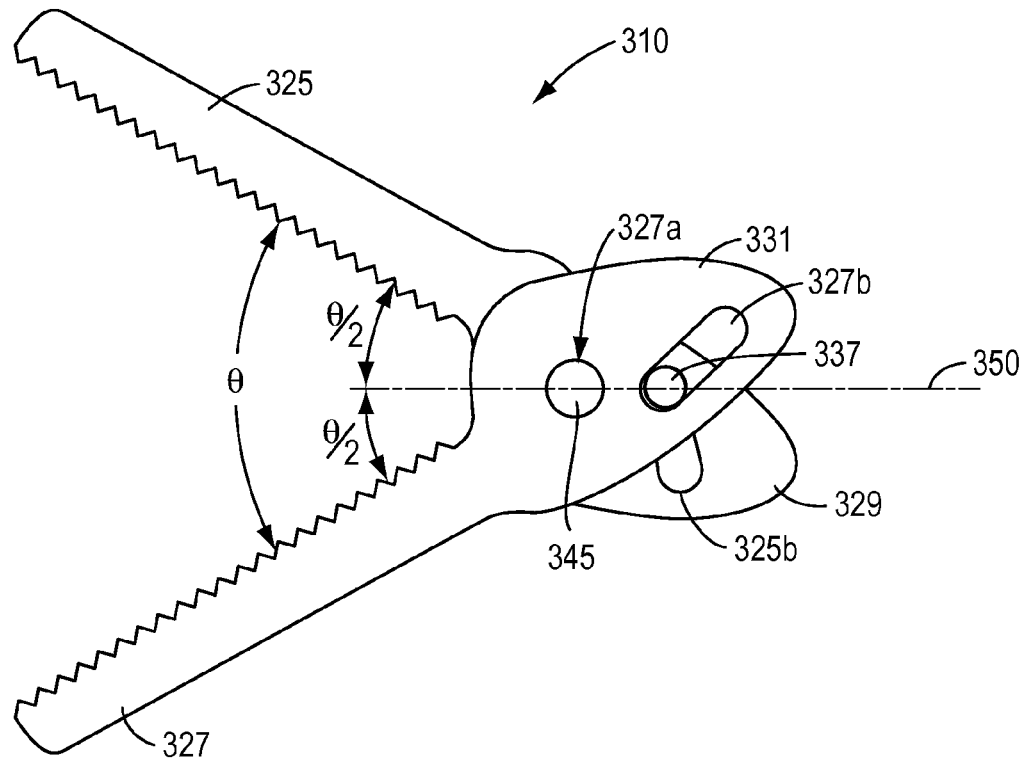
FIG. 3B is a side view of the jaw members of the exemplary end effector of FIG. 3A in accordance with the present teachings.
Figure 6A:
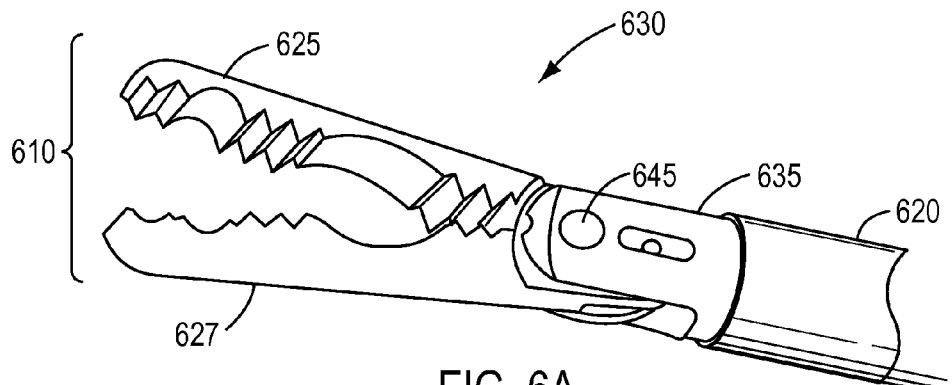
FIG. 6A is a perspective view of an alternative exemplary end effector for use in a surgical instrument in accordance with an exemplary embodiment of the present teachings.
Figure 6B:
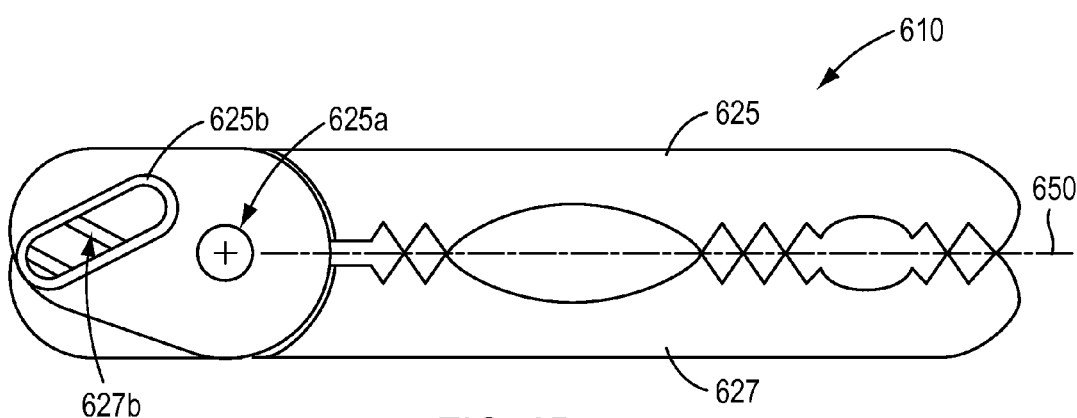
FIG. 6B is a side view of the jaw members of the exemplary end effector of FIG. 6A in a closed grip position in accordance with an exemplary embodiment of the present teachings.
Figure 6C:
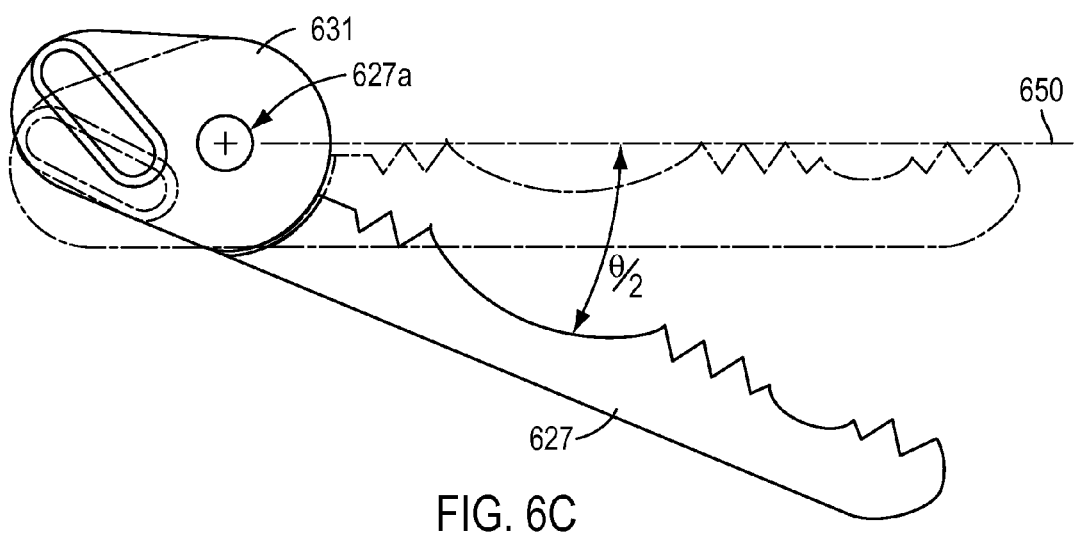
FIG. 6C is a side view of a single jaw member of the exemplary end effector of FIG. 6A moving from a closed grip position (shown in dashed lines) to an open grip position in accordance with an exemplary embodiment of the present teachings.
Figure 6D:
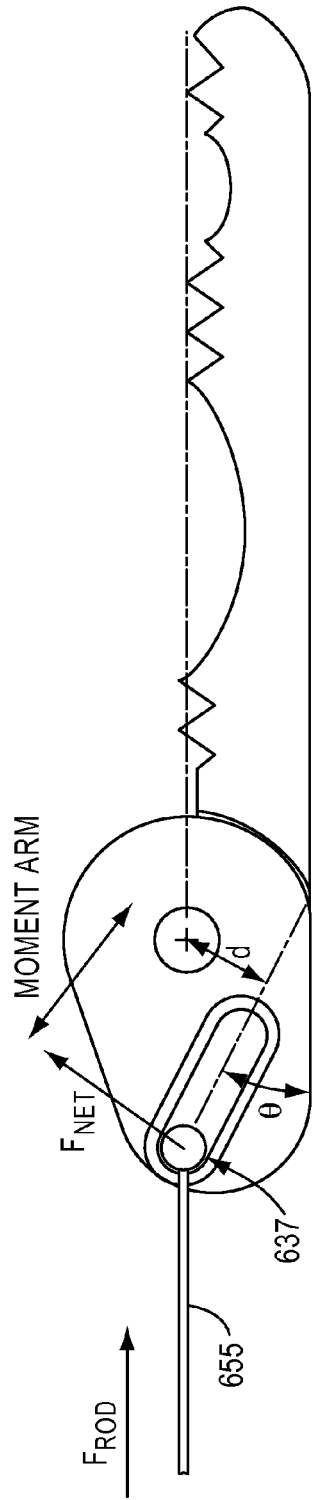
FIG. 6D is a force diagram illustrating the forces applied by a push-pull rod and acting on a jaw member of the exemplary end effector when the jaw member is in a closed grip position in accordance with an exemplary embodiment of the present teachings.
Figure 6E:
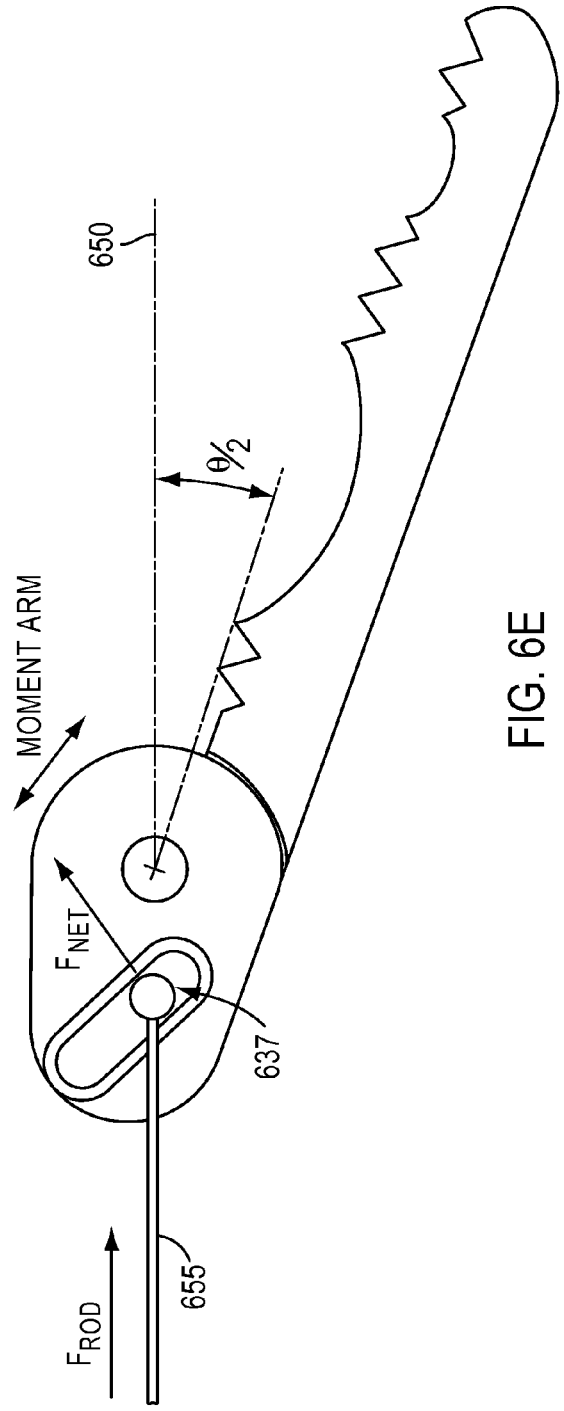
FIG. 6E is a force diagram illustrating the forces applied by a push-pull rod and acting on a jaw member of the exemplary end effector when the jaw member is in an open grip position in accordance with an exemplary embodiment of the present teachings.

With reference now to FIG. 3A, an exemplary embodiment of an end effector 300 for use with the instrument 200 is shown, although the end effector 300 is not limited thereto and may be any end effector configured for use to perform surgical procedures that require gripping and/or manipulating tissue. The end effector 300 may be provided with a gripping device, such as, for example, a pair of jaws 310 at the end of the instrument shaft 320. The jaws 310 may include a first jaw member 325 and a second jaw member 327 configured to move between an open position and a closed position. As illustrated in FIG. 3B, each jaw member may have a range of motion from about 0 degrees to about 30 degrees, providing a full range of motion for the jaws 310 from about 0 degrees to about 60 degrees. An angle θ is defined between the jaw members and is representative of the grip angle of the jaws. The distance between a centerline 350 of the jaws 310 and one of the respective jaw members 325, 327, represents half of the grip angle, or θ/2. When the jaw members are touching one another, such that both jaw members extend along centerline 350, the grip angle θ is approximately 0 degrees, and the jaws are in the closed position (see also FIG. 6B). When the jaw members are fully spaced away from one another, the jaws are in the open position, and the grip angle θ is approximately 60 degrees. The range of motion is intended to be exemplary only, and as one of skill in the art will understand, the range of motion of the end effector can be larger or smaller based upon the intended use of the instrument and may depend upon the structure of the jaw members, the manner of connection of the jaw members, and/or the manner of actuation of the jaw members.

As shown in FIG. 3B, each jaw member 325, 327 may include a proximal extension 329, 331 which is received within a clevis 335 (see FIG. 3A) that supports and connects the end effector 300 to the instrument shaft 320. A clevis pin 345 can extend through holes 340 in sides of the clevis 345 and through holes 325a, 327a in the jaw extensions 329, 331 to pivotally couple the jaw members 325, 327 and clevis 345 together, permitting the jaws to open and close as they pivot about the pin 345. In addition, the extensions 329, 331 may include cam slots 325b, 327b through which a pin 337 moves during the opening and closing of the jaws 310.

Figure 3C:
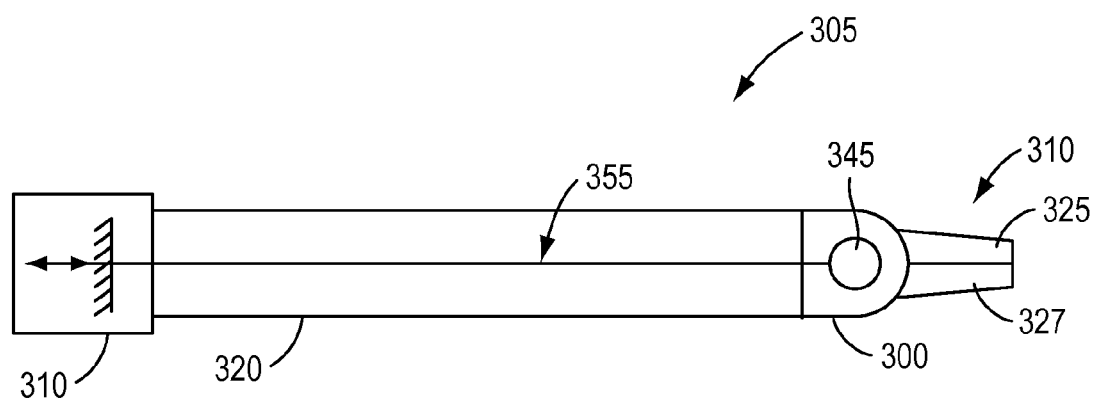
FIG. 3C is a diagrammatic view of a push/pull instrument design to be used with the exemplary end effector of FIG. 3A in accordance with an exemplary embodiment of the present teachings.
Figure 3D:
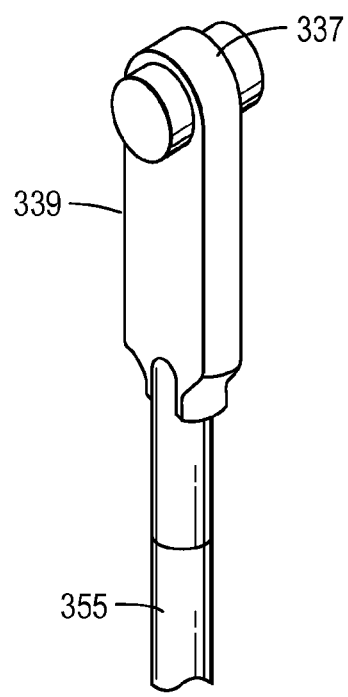
FIG. 3D is a perspective view of an exemplary embodiment of a drive element connector used to connect the end effector of FIG. 3A to a drive rod in accordance with an exemplary embodiment of the present teachings.

As illustrated in FIG. 3D, pin 337 may be attached to or form part of a distal end of a drive element, such as a drive rod connector element 339, which couples pin 337 to a push/pull rod 355. The jaw members 325, 327 may be actuated by push-pull rod 355. In such a "push/pull" design, a single compression/tension element may be used to move the end effector component. Pulling (tension) is used to move the component in one direction, and pushing (compression) is used to move the component in the opposite direction. In some implementations, the compression force is used to actuate the end effector component in the direction that requires the highest force (e.g., closing jaws). As shown in FIG. 3C, the push/pull rod 355 may extend proximally through instrument shaft 320 toward a proximal housing (not shown) of the instrument, receiving actuation forces from various drives (not shown) in a transmission mechanism 305 within the proximal housing that is attached to an actuation interface assembly of a patient side cart (e.g., as shown in FIG. 1A). The drive element(s) of the instrument can have a variety of forms and be implemented in various ways, exemplary arrangements and operations of which are disclosed, for example, in U.S. Pat. App. Pub. No. 2011/0071542 A1 (published Mar. 24, 2011), entitled "CURVED CANNULA SURGICAL SYSTEM," incorporated by reference herein.

In certain instances, the type of surgery to be performed and the type of access available to the surgical site may dictate the architecture of the surgical instrument used in a particular procedure. For example, tools that require flexibility to access the surgical site may have a simple mechanical actuation structure, such as the push-pull rod connected to the end effector of the surgical instrument as described above. Similarly, the type of surgery may dictate the type of end effectors used. For example, surgical access to a kidney or a gall bladder necessitates the use of end effectors forming a jaw having both sufficient size (i.e., length) and a sufficiently wide grip angle to grasp and manipulate the organs.

Figure 4:
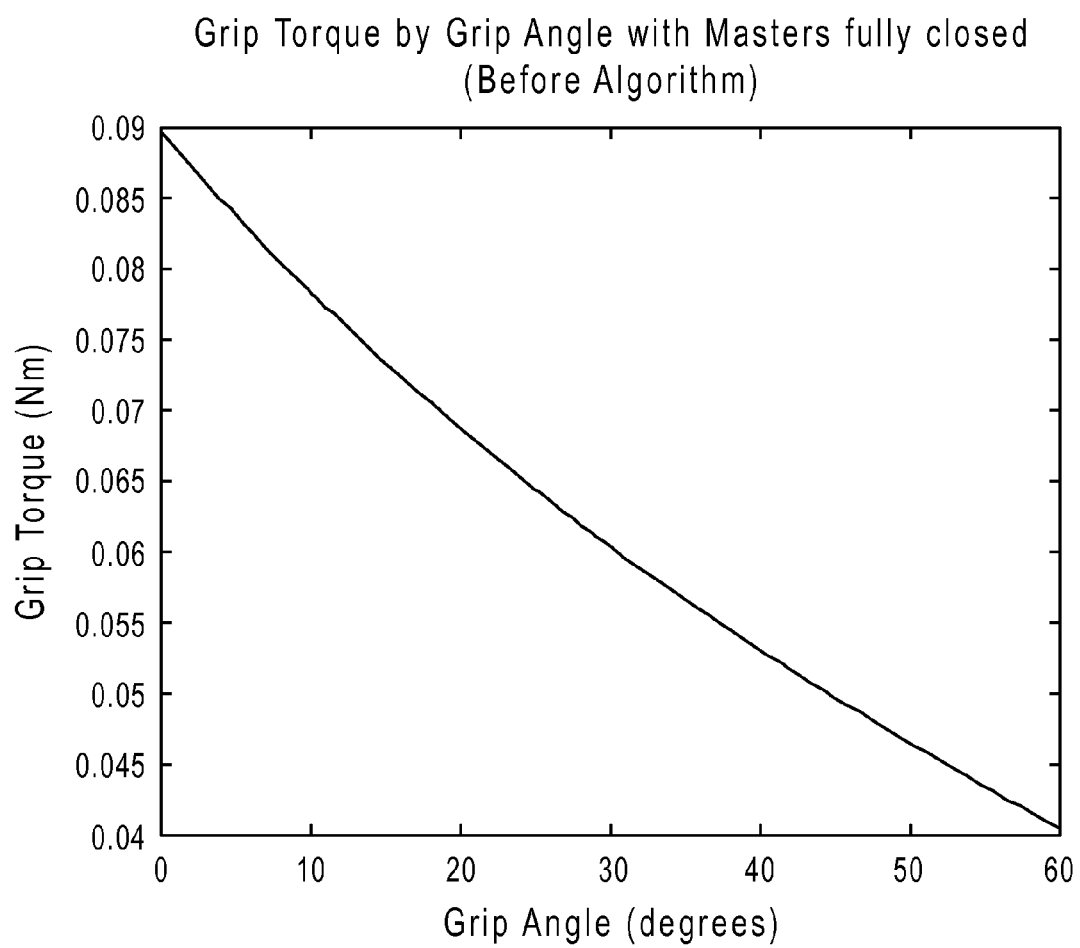
FIG. 4 is a graphical representation of conventional grip force applied by an end effector of a surgical instrument versus a measured (actual) position of the end effector for a given rod force applied by a manipulator.

In such instruments, as discussed above, the connection between the jaws of the end effector and the push rod may utilize cam slots in portions of the jaw elements, with a pin moving through the cam slots as the jaws articulate relative to one another to open and close the grip. Such a connection between the push rod and the end effector jaw leads to significant changes in mechanical advantage at different grip angles. The variation in mechanical advantage creates a significant difference in grip force at the jaws through a range of motion of the jaws. For example, as illustrated in the graph of FIG. 4, when a given force is applied to the push rod to actuate the jaws through a range of motion (e.g., from closed (0° angle between jaw elements) to open (60° angle between jaw elements)) a grip torque of the jaws can be approximately five times higher when the jaws are closed than when the jaws are open to their full extent. That is, when the same force is applied to a push-pull rod throughout a range of motion of the jaws, the grip force of the jaws can vary significantly throughout the range of motion. Clinically, this means that a rod force which applies a reasonable torque with the grips open (such as grasping a kidney) could damage tissue if applied with the grips closed.

In some cases, it may be undesirable to increase the grip torque applied by the jaws when the grip is closed. However, it may be desirable to increase the grip torque applied by the jaws when the grip is open. This would permit, for example, better grip strength when the jaws are grasping and/or manipulating a large tissue such as a kidney, where it may be desirable to have sufficient strength to grip the tissue without grasping it tightly. Thus, it may be beneficial to increase the grip force applied when the jaws are open while maintaining the grip force when the jaws are closed. It also may be beneficial to linearize the grip torques applied by the jaws across the range of motion of the jaws.

Figure 5:
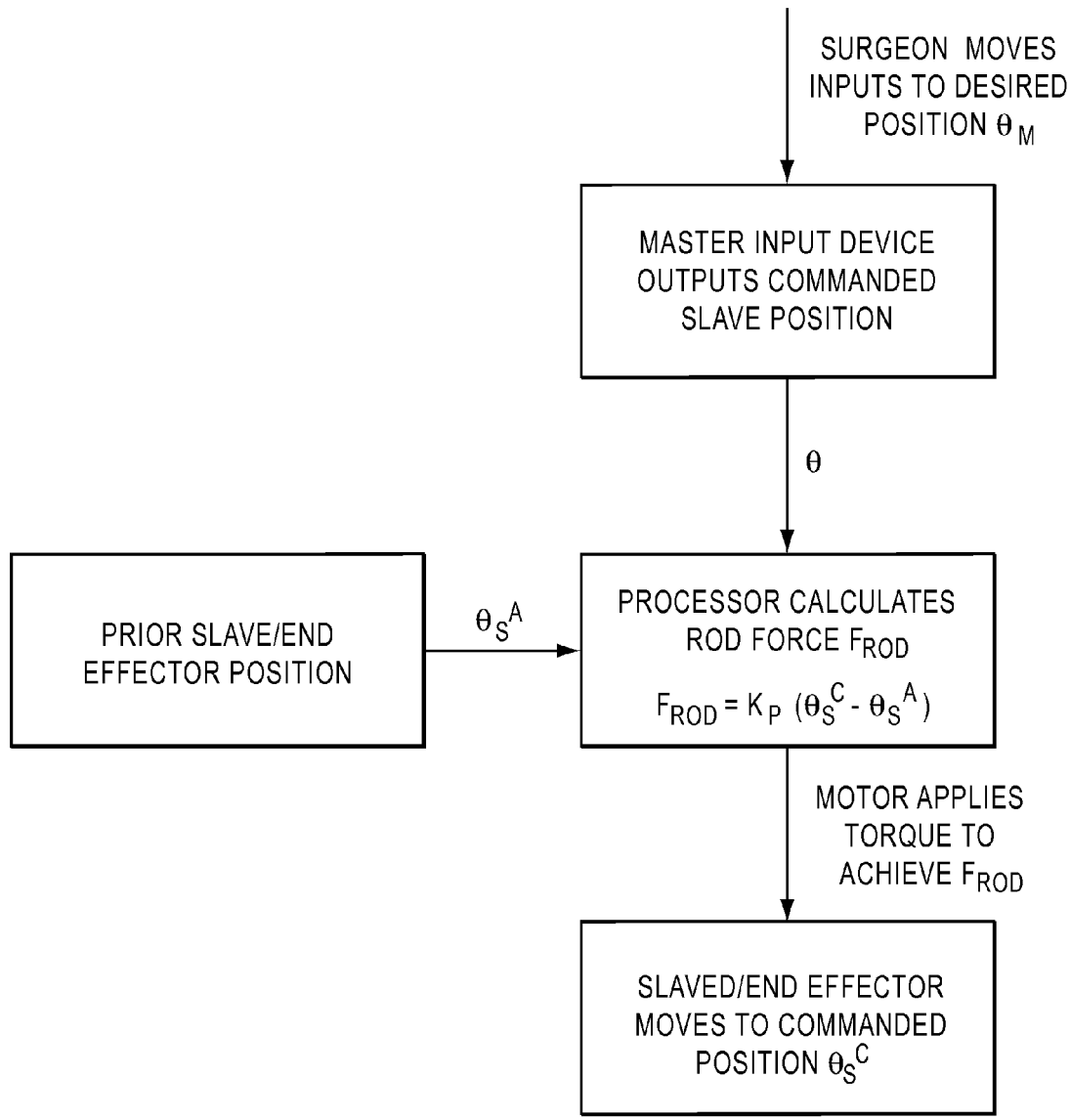
FIG. 5 is a functional block diagram schematically illustrating an exemplary master/slave arrangement for manipulating position and orientation of an end effector.

Referring now to FIG. 5, a reciprocal master/slave arrangement is used for actuation of manipulator arm 106 to provide orientation and positioning of end effector 230 in response to movement of pinchers 124a, 124b of the MTMs 122a, 122b. As used herein, the term master position, or master input position, is the actual position to which the surgeon or system controller moves the pinchers 124a, 124b. This position also may be referred to as the commanded position—the position to which the surgeon is commanding the end effector of the surgical instrument to move. As used herein, the term slave position refers to the position of the end effector of the surgical instrument. As described in the following examples, the master position and slave position are discussed with respect to the grip angle of the end effector. However, it should be understood that the various master and slave positions may comprise vectors (in Cartesian space, polar space, joint space, or the like) as well as simple angles or linear separations, and the kinematic chains of the master and slave may be quite different, often even having different degrees of freedom.

In general, the actual configuration of the master and slave will be measured using potentiometers, encoders, or other position, velocity, and/or acceleration sensors affixed to rotational joints of the input control devices and slave manipulator. Position information may also be provided by encoders and/or potentiometers affixed to the set-up joints of the system 100, which may include both rotational joints and linear sliding joints (particularly for the vertical axis). A variety of alternative configurations for the input mechanisms might be used, including stepper motors, optical configuration recognition systems (for example, using light emitting diodes mounted to the surgical tools and a CCD/frame grabber optical processing system coupled to the endoscope), and the like. It should also be understood that this direct master/slave arrangement will often provide uniform following forces throughout the range of the motion of the master and/or slave, regardless of whether the following forces are applied using a system having a single degree of freedom, or a complex input control device and slave mechanism having six degrees of freedom for both the master and slave (optionally even including redundant degrees of freedom for the master and/or slave to avoid singularities).

As illustrated schematically in FIG. 5, a master input device 122 defines an actual master position $\theta_M$ of the pincher assembly. This actual position of the master $\theta_M$ represents the position to which the surgeon or other system operator has moved the input device and also represents the position to which the surgeon or other system operator is commanding the jaws of the end effector to move (the desired or commanded position of the end effector). Thus, this position is fed into the controller as a commanded or desired slave (end effector jaws) position $\theta_S^C$. The amount of force applied by the end effectors will vary with the difference between the commanded/desired position of the slave (end effector jaws) $\theta_S^C$ and the actual position of the slave (end effector jaws) $\theta_S^A$, with the following force on the end effector jaws increasing with increasing misalignment between the actual and desired positions, often with a proportional relationship.

However, in cases where the mechanical advantage of the instrument is not linear, the force applied to the end effector also is not linear, resulting in a grip torque that varies widely through a range of motion of the end effectors for a given rod force. The force applied to a push-pull rod to actuate an end effector can be calculated using the proportional feedback equation:

$$F_{rod}=K_P(x_d-x_m) \quad (1)$$

where $F_{rod}$ is the force along the rod, $K_p$ is the proportional gain, $x_d$ is the commanded (desired) position of the grip and $x_m$ is the measured (actual) position of the grip. In the proportional control algorithm, the controller output is proportional to the error signal, which is the difference between the commanded position of the end effector jaws and the measured or actual position of the end effector jaws. In other words, the output of the proportional controller is the multiplication product of the error signal and the proportional gain.

FIGS. 6A-6E illustrate another exemplary embodiment of an end effector 600 having a mechanical advantage. Similar to the end effector illustrated in FIGS. 3A-3D, the end effector 600 utilizes a cam slot and pin construction to achieve actuation of the jaws 610 of the end effector. As illustrated in the force diagrams of FIGS. 6D and 6E, and as illustrated in the graph of FIG. 4, the change in mechanical advantage as the end effector jaws move from the closed position, e.g., 0 degrees, to the open position, e.g., 60 degrees, results in a significant difference in grip torque being applied at the open and closed positions by jaws 610. In particular, grip torque $\tau_{GRIP}$ can be calculated as a function of rod force $F_{rod}$, grip angle of the jaws $\theta$, angle of the cam slot $\varnothing$, and the distance d the cam slot is offset from the center of rotation of the jaws. The calculations to determine $\tau_{GRIP}$ may be characterized as multiplying the net force acting on the jaws, $F_{NET}$, by the moment arm M.A., resulting in the following equation:

$$\tau_{GRIP}=(F_{ROD}*d*\cos(\varnothing+\theta))/(\sin^2(\varnothing+\theta)). \quad (2)$$

As illustrated in FIG. 4, the grip torque may be approximately five times greater when the grips are closed (e.g., $\theta=0$) than when the grips are fully open (e.g., $\theta=60$). In order to compensate for this difference, and to make the grip force more linear throughout the range of motion of the grips, several solutions are possible. For example, the inventor contemplated that it would be possible to make the proportional gain be a function of either the commanded position of the end effector jaws or of the measured (actual) desired position of the end effector jaws. While offering a solution to the linearization of the grip force, it is possible that a dynamically changing gain could introduce instability into the system. Additionally, such changes could require a change to the system architecture. Another alternative solution would be to change the mechanical structure of the cam slot to reduce the mechanical advantage. However, redesign of instruments could potentially reduce the mechanical advantage. Utilizing the techniques for compensating for the grip force differential according to various exemplary embodiments can provide for a mathematical/algorithm solution that does not introduce instability into the system and does not require a redesign of system components. Such a solution may take into account the mechanical structure of the instrument, the desire to keep grip force applied by the grips, when closed, the same, and the desire to increase the grip force applied by the grips, when the grips are not closed.

Figure 7:
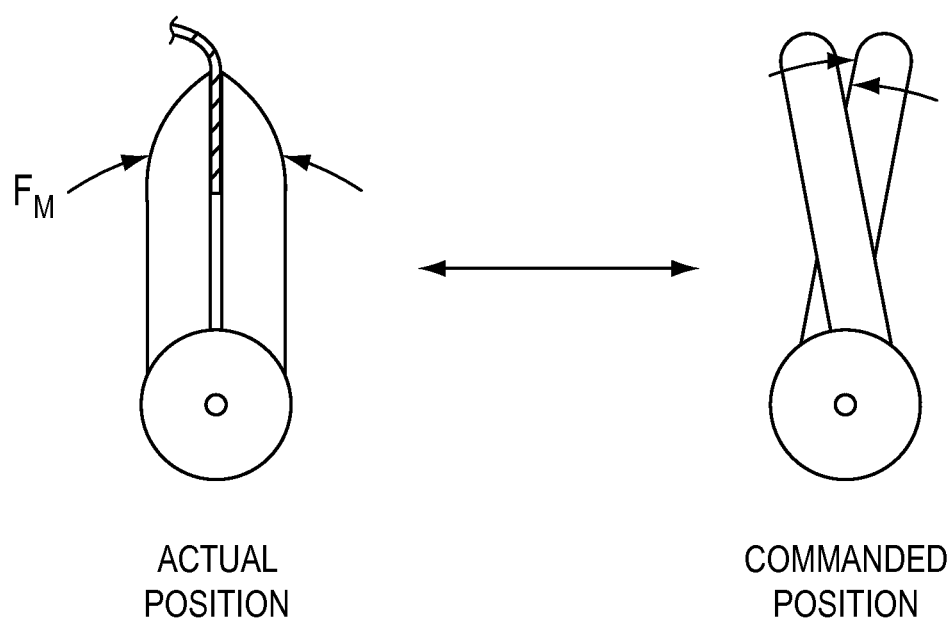
FIG. 7 is a schematic representation of a master (commanded) position of an input device and slave (actual) position of an end effector jaw in accordance with the present teachings.

Although the grips are fully closed when the grip angle $\theta=0$, it is necessary to allow a user of the system to command the grips to a position less than zero, i.e., to a negative position, in order to apply force with grips when they are closed. This is illustrated in FIG. 7.

Figure 8:
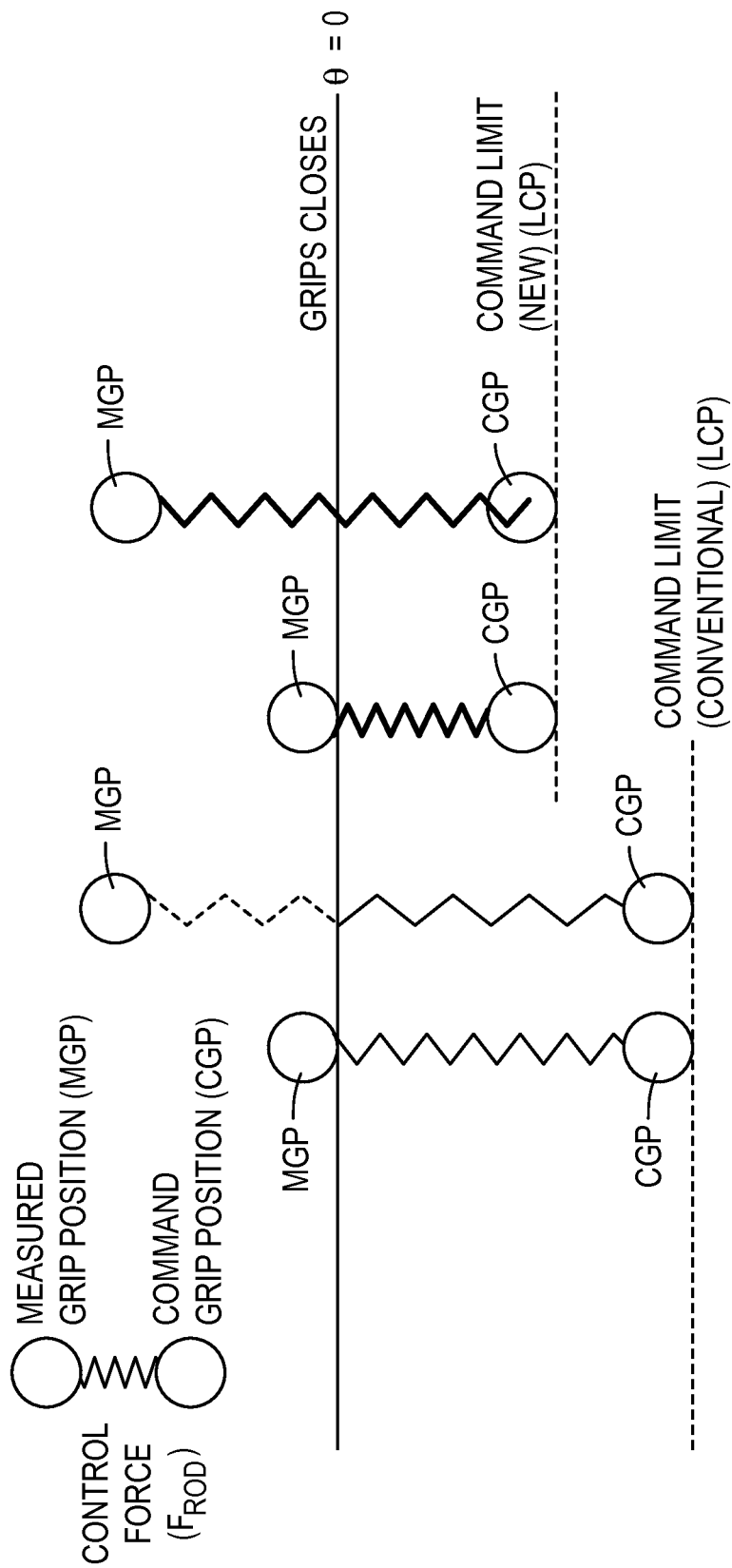
FIG. 8 is a diagrammatic schematic representation of a spring model representing raising a lowest commanded position of a grip and increasing spring stiffness to linearize to increase force applied to a push rod of a surgical instrument by a manipulator of the surgical system in accordance with the teachings of the present invention.

One manner in which this problem can be visualized or modeled is with a spring. As illustrated in FIG. 8, the grip angle $\theta$ is the point at which the grips are closed (just touching one another). In order to permit a user to command grip force at a closed grip position, a software application running on system 100 sets a floor or command limit below 0. This floor may be referred to as the lowest commanded position ("LCP") of the grip. To calculate the force applied to the rod to when the grips are closed (measured position=0), equation 1 may be used. In such a calculation, the commanded position $x_d$ for grips=0 is represented by the floor or limit set by the system. That is, the force can be visualized as the force necessary to move the grip (represented by CPG) from the conventional command limit position to the actual closed grip position identified as MPG.

If the standard instrument calculations have $K_p=10$ N/° and a minimum value of $x_d=-25°$, the force on the rod when the grip is closed ($x_m=0°$) is:

$$F_{rod}=K_P(X_d-X_m)=10(-25-0)=-250N$$

In order to maintain the same grip force when the grips are closed but increase the grip force when the grips are open, it is necessary to increase the rod force (motor torque) as the grips open. Referring to the spring model of FIG. 8, it is possible to increase this force by strengthening the spring. That is, the greater the distance the spring is stretched, the greater the force that is required to stretch the spring. This can be represented mathematically by increasing the proportional gain ($K_P$). However, increasing the proportional gain, without affecting other changes, will increase the grip force not only when the grips are opened, but also when the grips are closed.

Various exemplary embodiments, therefore, contemplate simultaneously changing the minimum commanded position $x_d$ and the proportional gain $K_p$, while the force on the drive rod is kept the same when the grips are closed and increased when the grips are open. Such a simultaneous change does not introduce a dynamically changing gain into the system.

Thus, as illustrated in FIG. 8, a new command limit $x_d$ may be set as the LCP, wherein the lower limit of $x_d$ is reduced. In one exemplary embodiment, the lower limit of $x_d$ may be reduced by a factor of five. Reducing the lower limit in such a manner reduces the position error between the commanded position and the actual position of the grips by a factor of five as well. In order to compensate for this decrease, and to keep the grip torque the same when the grips are closed, the proportional gain can be increased by a factor of five. Since the position error for open grip does not decrease by the same factor as the LCP, the force on the rod is increased with a resulting increase in grip torque.

In the example calculation above, the command limit for $x_d=-25°$. If the command limit is reduced by a factor of five, then $x_{dnew}=-5°$. Increasing the proportional gain by a factor of five raises $K_p=10$ N/° to $K_{pnew}=50$ N/° and the force on the rod when the grip is closed is:

$$F_{rodnew}=K_{Pnew}(x_{dnew}-x_m)=50(-5-0)=-250N$$

thus resulting in the same force prior to the changes to the LCP and proportional gain.

However, when comparing the force on the rod when the grip is open ($x_m=60°$) the results are:

$$F_{rod}=K_P(x_d-x_m)=10(-25-60)=-850N$$

$$F_{rodnew}=K_{Pnew}(x_{dnew}-x_M)=50(-5-60)=-3250N$$

Figure 9:
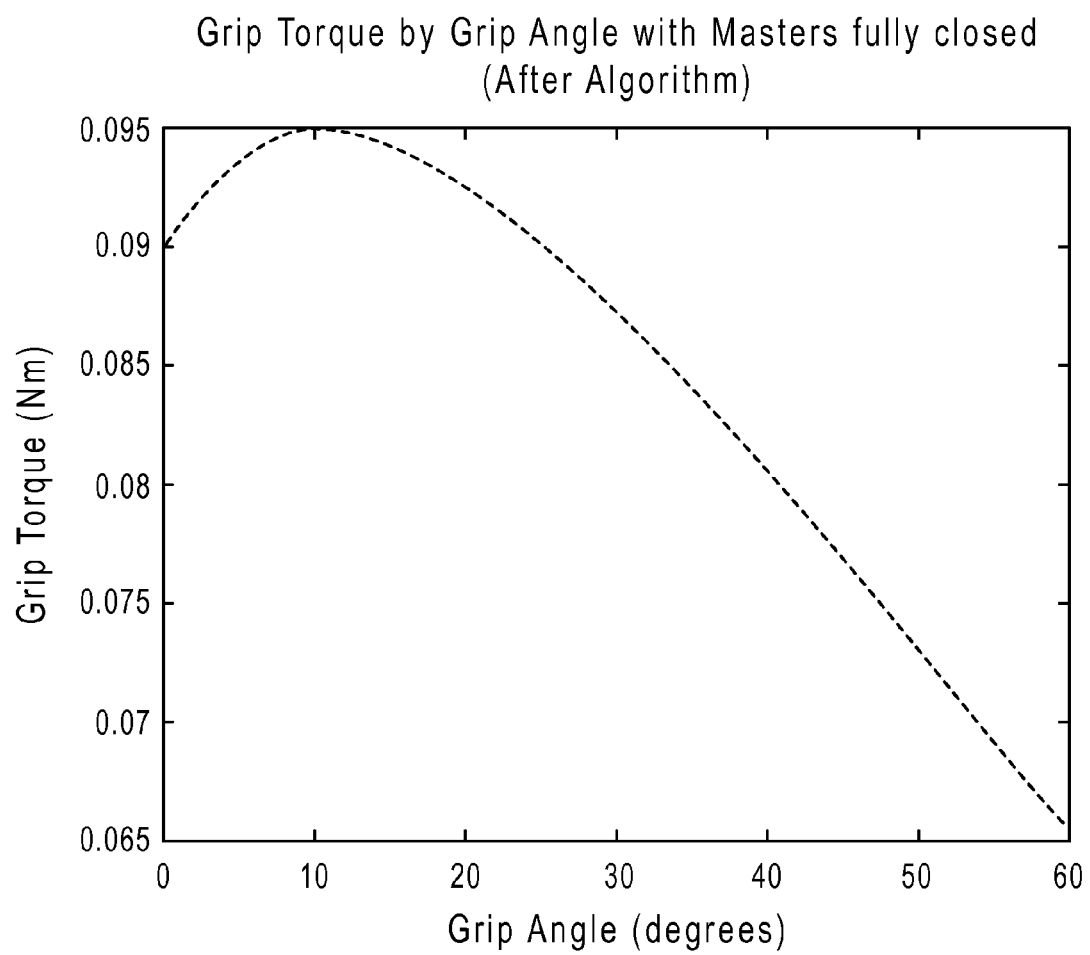
FIG. 9 is a graphical representation of representation of a linearized grip force applied by an end effector of a surgical instrument in accordance with the present teachings versus a measured (actual) position of the end effector for a given rod force applied by a manipulator in accordance with the present teachings.

As illustrated in FIG. 9, the curve for the grip torque applied through a range of motion of 0 degrees to 60 degrees, while not exactly linear, is substantially flattened out, with the resultant difference in grip forces between the closed and open grip positions being reduced by a factor of about three (3). In particular, as shown in FIG. 9, the largest increase in the grip force is found when the grips are only slightly open and/or substantially closed (e.g., at between about 0 degrees and 20 degrees). The measured increase in grip torque differs from the theoretical calculation due to mechanical compliance in the drive train between the motor/sensor and the instrument jaws. When the surgeon grasps something with the grips wide open and applies a grip force, the compliance will lead to the sensor reading a slightly closed grip angle. With the increased torque of the improved algorithm, the difference between the measured and commanded position ($x_{dnew}-x_M$) will be less than prior to the algorithm ($x_d-x_M$), partially reducing the improvement in grip torque. Although the command limit is decreased by a factor of five and the proportional gain increased by a factor of five in the above example, one of ordinary skill in the art will recognize that this teaching can be applied to increase grip force for a variety of tools, and depending upon the structure of the tool, the mechanical advantage of the tool, the desired change in grip force, the amount by which the command limit is decreased and the proportional gain is increased may vary. Indeed, it is possible that the command limit may be decreased by one factor while the proportional gain is increased by a different factor. It is also possible that a clinical application may call for more grip force when the grips are closed than when open, such as for clamping firmly on small tissue, in which case the process can be inverted to increase the command limit and decrease the proportional gain.

As discussed above, various exemplary embodiments contemplate being implemented within an existing system architecture. That is, a tool having a changing mechanical advantage can be plugged into an existing teleoperated surgical system, and the surgical system can recognize the features of the instrument and apply the appropriate corrections to substantially linearize grip force through a range of motion of the end effectors.

To facilitate such a solution, the instrument memory may include particular values that can be employed in control algorithms, such as tool compliance and gain values, in order to permit full utilization of the instrument. For example, an instrument memory may include a grip compliance value that is based on instrument architecture, elasticity of the system (such as elasticity of the instrument shaft), and loss of mechanical advantage. In addition, the memory may store a stiffness value/gain value.

Figure 10:
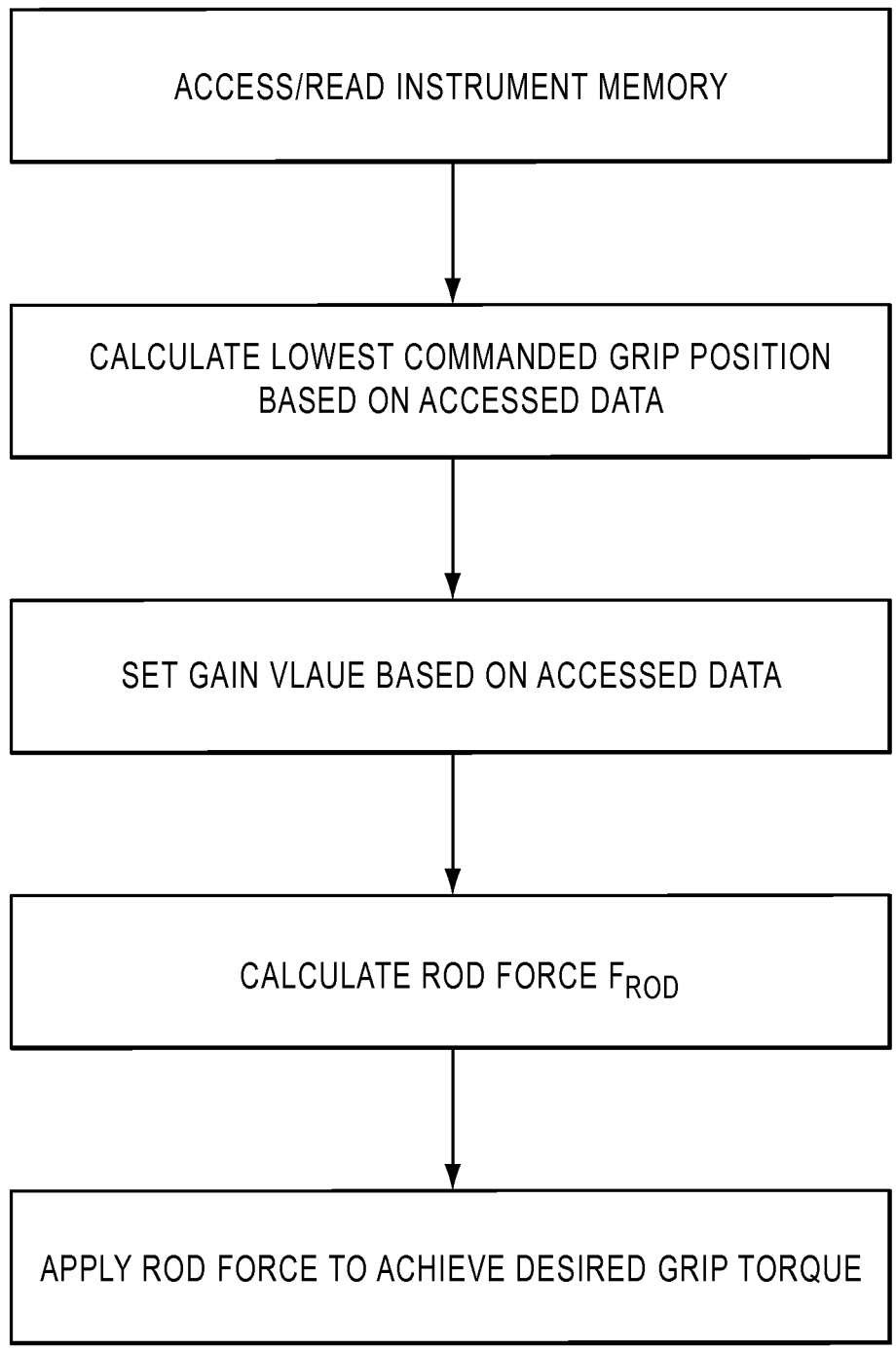
FIG. 10 is a flow chart illustrating a method of linearizing grip torque through a range of grip angles for a given rod force in accordance with the present teachings.

Thus, as illustrated in the flow diagram of FIG. 10, when a new instrument is connected to manipulator arm 106, the central processing unit 142 may access the instrument memory and read the values stored on the memory that are associated with that particular instrument. After reading the memory, the processing unit 142 may calculate a new lower limit for the commanded position or lowest commanded position ("LCP") $x_d$ for that instrument. The processing unit also may store stiffness value/gain value associated with the instrument as a new proportional gain value $K_P$. These new values will be used to calculate the rod force $F_{rod}$ to be applied to the push/pull rod 355 when the central processing unit 142 receives input from the MTM 122 providing a commanded position for the end effector.

As set forth in the flow chart of FIG. 5, the surgeon's input through the MTMs will be fed into the central processing unit 142 as a commanded or desired slave position $\theta_S^C$ (commanded position of the end effector). The processor will determine or access a stored value for the actual position of the end effector $\theta_S^A$. Using these values, the rod force will be calculated using equation 1: $F_{rod}=K_p(x_d-X_m)$, where $x_d=\theta_S^C$ and $x_m=\theta_S^A$. If the grips are closed, the value of $x_d$ will be equal to the value of the LCP calculated by the processor after accessing the instrument memory. Similarly, for all calculations, the value of $K_p$ will be equal to that identified by the processor as associated with the specific tool attached to manipulator arm 106. The motors will apply a torque to apply the calculated rod force $F_{rod}$ to the push/pull rod via the force transmission mechanism, resulting in the application of a grip force by the end effectors of the surgical instrument.

Modifications that would provide additional and alternative solutions will be apparent to one of ordinary skill in the art based on the teachings herein. For example, rather than calculating the rod force for each input, it would be possible to provide processing unit 142 with a lookup table listing a force to be applied for each grip angle. Such a lookup table may be associated with the instrument memory or with the central processing unit itself. Additionally or alternatively, it would be possible to adjust the stiffness of the spring (i.e., the gain) based on the actual position of the grip rather than the commanded position. It also would be possible to make the rod force a function of the grip angle, or to control the rod force based on jaw force (see, for example, U.S. Patent Application Publication No. 2010/0087835 published on Apr. 8, 2010 and entitled "Wireless Force Sensor on a Distal Portion of a Surgical Instrument and Method," the entire contents of which are incorporated herein by reference.

In another alternative exemplary embodiment, it may be possible to change the LCP and/or the gain at a specific threshold. For example, rather than setting LCP and gain upon engagement of the instrument with the manipulator arm, it is possible to set these values when a certain grip angle is reached. Thus, for example, for a tool that has a dramatically changing mechanical advantage over a first grip range of motion and a relatively reduce mechanical advantage over a second grip range of motion, it may be desirable to linearize the grip force over only the first grip range of motion, or it may be desirable to use differently variables to create different linearization for the first range and the second range.

As another alternative, the force linearization may be used to provide fine force control when a delicate grip is necessary. In such an instance, the values for LCP and $K_p$ may be changed only for the range of motion where fine control is need. For example, such a control could be employed when a grip angle of, for example, 10-30 degrees is commanded.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary and elements within different embodiments may be used with one another. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the present teachings and does not pose a limitation on the scope of the present teachings unless otherwise claimed. No language in the specification should be construed as indicating any non-claimed element as essential to the practice of the present teachings.

It is to be understood that the particular examples and embodiments set forth herein are non-limiting, and modifications to structure, dimensions, materials, and methodologies may be made without departing from the scope of the present teachings. Other embodiments in accordance with the present disclosure will be apparent to those skilled in the art from consideration of the specification and practice of the present teachings disclosed herein. It is intended that the specification and examples be considered as exemplary only, with a true scope and spirit being indicated by the following claims.

What is claimed is:

1. A method for controlling grip force of an end effector of a surgical instrument, the method comprising:
    receiving a first input signal indicative of a commanded position of a gripping element of the surgical instrument end effector;
    outputting an actuation signal to apply a changing grip actuation force to actuate the gripping element to cause the end effector to exert a grip force, wherein the actuation signal is based at least in part on the first input signal, an actual position of the gripping element, and a variable mechanical advantage of the surgical instrument end effector, the mechanical advantage varying with the actual position of the gripping element; and
    in response to the actuation signal, actuating the gripping element to cause the end effector to exert the grip force.

2. The method of claim 1, further comprising accessing at least one instrument parameter stored on a storage device of a surgical instrument.

3. The method of claim 2, wherein outputting the actuation signal comprises outputting an actuation signal based at least in part on the at least one instrument parameter.

4. The method of claim 2, further comprising limiting a range of the commanded position of the gripping element.

5. The method of claim 4, wherein limiting a range of the commanded position comprises reducing a lower end of the range of the commanded position.

6. The method of claim 2, wherein accessing at least one instrument parameter comprises accessing information related to at least one of a mechanical compliance of the surgical instrument, a mechanical advantage of the surgical instrument, a desired proportional gain, and a range of permissible commanded positions of the gripping element.

7. The method of claim 2, wherein:
    outputting the actuation signal further comprises implementing proportional control logic, and
    wherein an initial proportional gain value used in the proportional control logic is set based on the at least one instrument parameter.

8. The method of claim 1, wherein the actuation signal is based at least in part on an error signal, the error signal being based on a difference between the commanded position of the gripping element and the actual position of the gripping element.

9. The method of claim 1, wherein outputting the actuation signal further comprises:
    implementing proportional control logic using a proportional gain value, and
    modifying the proportional gain value used in the proportional control logic to control the grip force.

10. The method of claim 1, wherein the first input signal indicative of a commanded position of the gripping element of the surgical instrument end effector is generated in response to input at a master grip input mechanism.

11. The method of claim 1, further comprising receiving a second input signal indicative of the actual position of the gripping element.

12. A teleoperated surgical system, comprising:
    a master grip input device;
    a surgical instrument having an end effector comprising a gripping element;
    a servomechanism operatively coupled to the end effector to apply a force to the end effector;
    at least one processor operatively coupling the servomechanism to the master grip input device to transmit a grip actuation force to actuate the gripping element to cause the end effector to exert a grip force in response to input at the master grip input device, the grip actuation force being based at least in part on a variable mechanical advantage of the surgical instrument end effector, the mechanical advantage varying with an actual position of the gripping element.

13. The surgical system of claim 12, wherein:
    the surgical instrument further comprises a storage device configured to store at least one instrument parameter,
    the at least one processor is configured to access the at least one instrument parameter stored by the storage device, and the grip actuation force is based at least in part on the at least one instrument parameter.

14. The surgical system of claim 13, wherein the at least one instrument parameter includes one of information indicative of at least one of a mechanical advantage of the end effector, an instrument compliance, a desired proportional gain, and a permissible range of commanded positions of the gripping element.

15. The surgical system of claim 13, wherein the at least one processor is further configured to constrain a commanded position of the gripping element based on the at least one instrument parameter.

16. The surgical system of claim 12, wherein the master grip input device is configured to output a signal indicative of a commanded position of the gripping element based on input at the master grip input device, and wherein the grip actuation force is based at least in part on the commanded position.

17. The surgical system of claim 16, wherein the signal indicative of the commanded position is limited by a permissible range of commanded positions of the gripping element.

18. The surgical system of claim 12, wherein the surgical instrument is configured to output a signal indicative of a measured position of the gripping element, and wherein the grip actuation force is based at least in part on the measured position.

19. The surgical system of claim 18, wherein the at least one processor is configured to output an error signal, the error signal being based on a difference between a commanded position of the gripping element and the measured position of the gripping element,
   wherein the commanded position is based on input at the master grip input device, and
   wherein the grip actuation force is based at least in part on the error signal.

20. The surgical system of claim 12, wherein the at least one processor is configured to implement proportional control logic to apply the grip actuation force, the proportional control logic being based in part on a desired proportional gain and a permissible range of commanded positions of the gripping element, the commanded position of the gripping element being based on input at the master grip input device.

* * * * *